(12) United States Patent
Kempe et al.

(10) Patent No.: US 8,908,174 B2
(45) Date of Patent: Dec. 9, 2014

(54) APPARATUS, ESPECIALLY MICROSCOPE, FOR THE ANALYSIS OF SAMPLES

(75) Inventors: Michael Kempe, Jena (DE); Gerhard Krampert, Jena (DE); Ingo Kleppe, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 551 days.

(21) Appl. No.: 13/121,919

(22) PCT Filed: Sep. 22, 2009

(86) PCT No.: PCT/EP2009/006817
§ 371 (c)(1),
(2), (4) Date: Mar. 30, 2011

(87) PCT Pub. No.: WO2010/037486
PCT Pub. Date: Apr. 8, 2010

(65) Prior Publication Data
US 2011/0174986 A1 Jul. 21, 2011

(30) Foreign Application Priority Data
Sep. 30, 2008 (DE) .................. 10 2008 049 886

(51) Int. Cl.
G01J 3/28 (2006.01)
G02B 21/16 (2006.01)
G02B 21/00 (2006.01)
G01N 21/64 (2006.01)

(52) U.S. Cl.
CPC ............ *G01N 21/6428* (2013.01); *G02B 21/16* (2013.01); *G01N 2021/6417* (2013.01); *G02B 21/0076* (2013.01); *G01N 21/6458* (2013.01)
USPC ......................................... 356/317

(58) Field of Classification Search
USPC ........................................... 356/317–318, 417
See application file for complete search history.

(56) References Cited

U.S. PATENT DOCUMENTS 6,025,956 A 2/2000 Nagano et al.
6,633,432 B2 * 10/2003 Iketaki ..................... 359/386
(Continued)

FOREIGN PATENT DOCUMENTS

DE 866 408 C 2/1953
DE 10155002 A1 5/2003
(Continued)

OTHER PUBLICATIONS

Klar, et al.;"Breaking Abbe's diffraction resolution limit in fluorescence microscopy w/ stimulated emission. . . ";Physical Review E. 2001;64(066613):1-9.
(Continued)

*Primary Examiner* — Kara E Geisel
(74) *Attorney, Agent, or Firm* — Duane Morris LLP

(57) ABSTRACT

A microscope device which has a diffraction-limited resolution volume, with multiple dye molecules that can be switched between different states, at least one of which is fluorescent. The fluorescence is focused using an objective lens and is imaged onto a spatially resolving detector. In at least one portion of the sample, the dye molecules have a distribution density that is greater than the inverse of the diffraction-limited resolution volume. One or more light sources are provided for emitting a switching radiation in order to switch a first subset of the dye molecules in the sample, and for emitting an excitation radiation in order to excite the first subset of dye molecules. A phase mask which generates a light distribution having an at least partially limited local minimum radiation on the detector plane is provided in the beam path, preferably in the detection beam path.

3 Claims, 11 Drawing Sheets

(56) References Cited

U.S. PATENT DOCUMENTS

| | | |
|---|---|---|
| 2004/0184144 A1 | 9/2004 | Goodwin |
| 2005/0046818 A1 | 3/2005 | Neil et al. |
| 2008/0068588 A1* | 3/2008 | Hess et al. .................. 356/36 |
| 2008/0158551 A1 | 7/2008 | Hess |
| 2008/0182336 A1 | 7/2008 | Zhuang et al. |
| 2009/0134342 A1 | 5/2009 | Hell et al. |

FOREIGN PATENT DOCUMENTS

| | | |
|---|---|---|
| DE | 10257237 A1 | 6/2003 |
| DE | 10 2006 04791 A1 | 4/2008 |
| EP | 1 985 995 A2 | 10/2008 |
| WO | WO 97/06509 | 2/1997 |
| WO | WO 98/45745 | 10/1998 |
| WO | WO 2006/127692 | 11/2006 |
| WO | WO 2008/032096 A2 | 3/2008 |

OTHER PUBLICATIONS

Notification of Transmittal of Copies of Translation of the International Preliminary Report on Patentability—Form PCT/IB/338, Apr. 14, 2011.

International Preliminary Report on Patentability—Form PCT/IB/373, Apr. 5, 2011.

Written Opinion of the International Searching Authority—Form PCT/ISA/237, Apr. 2011.

* cited by examiner

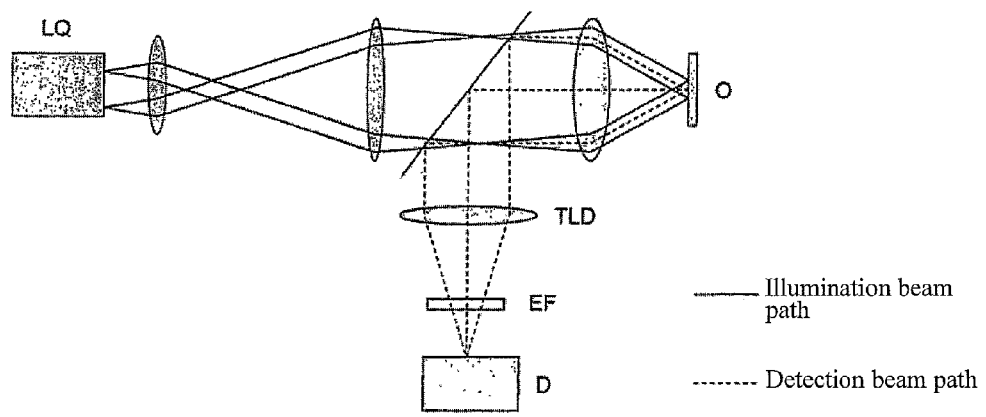
Figure 1: Prior art - TIRF illumination
LQ Light source
TLB Tube-body lens illumination
OL Objective lens
O Object
ST Beam splitter
TLD Tube-body lens detection
EF Emission filter
D Detector

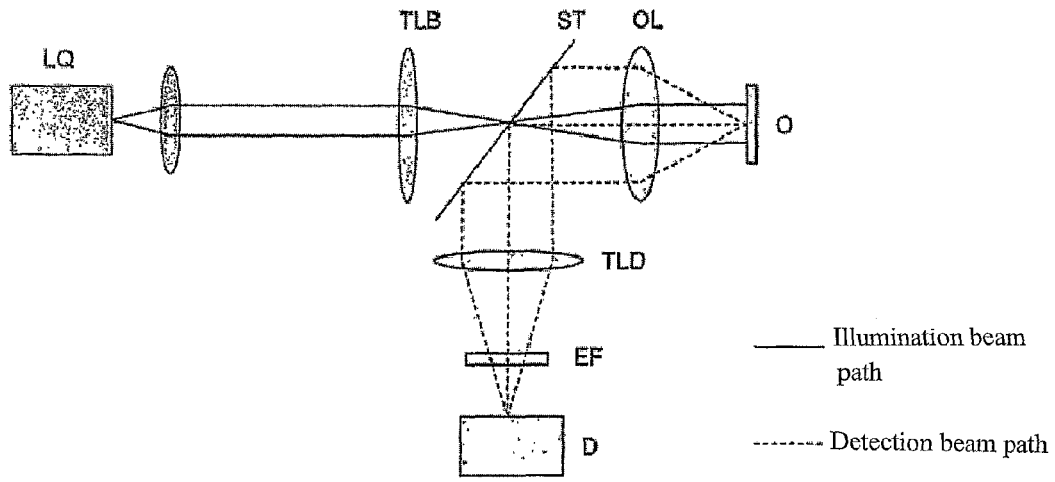
Figure 2: Prior art - far-field illumination
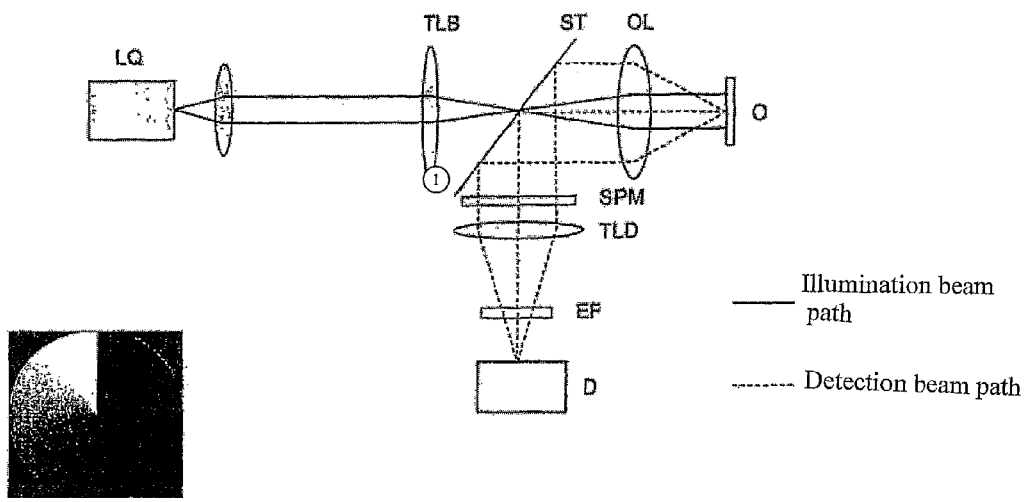
Phase profile in grayscale coding
(0 = white, $2\pi$ = black)
Figure 3: Doughnut – PSF
SPM Spiral phase mask

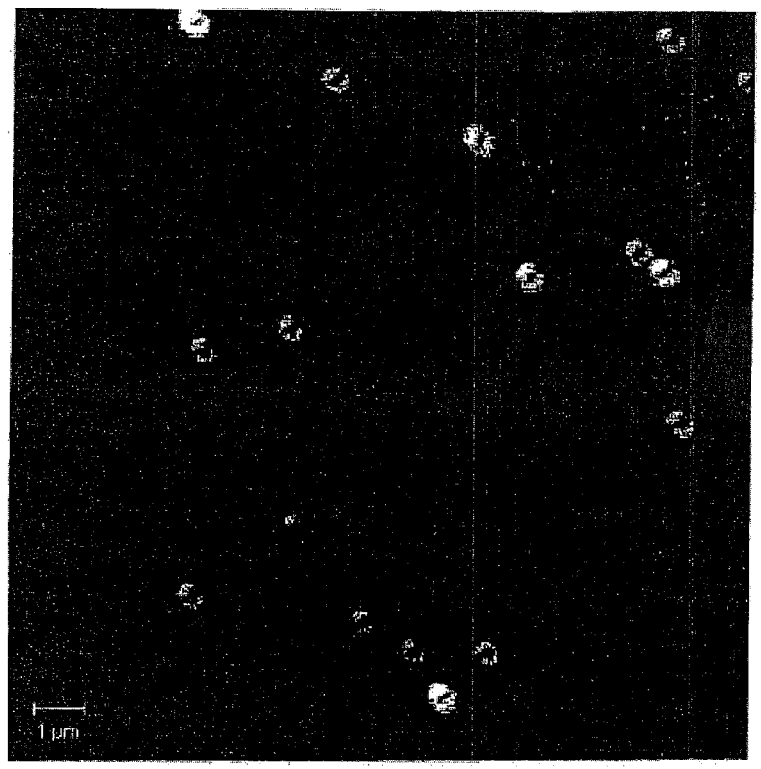
Figure 3a: PAL-M mapping with doughnut - PSF

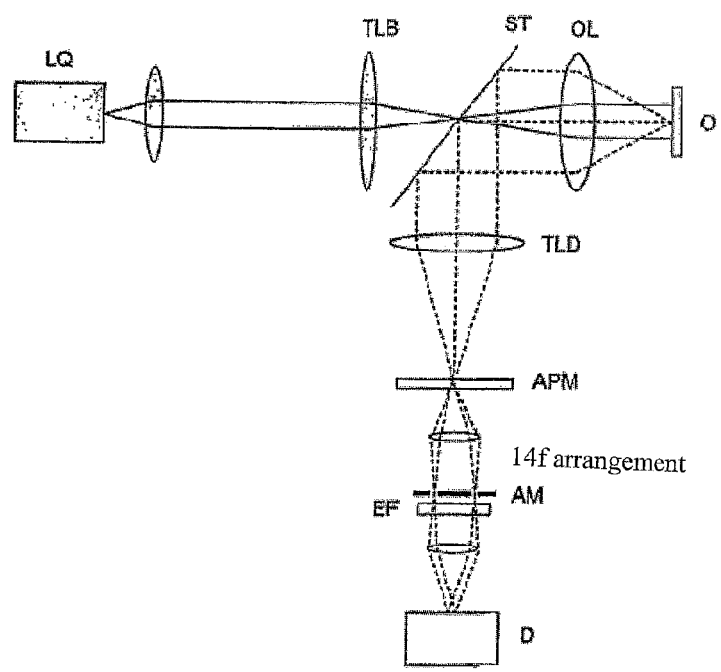
Figure 4: Bessel - PSF
APM: Axicon phase mask
AM: (Optional) aperture mask

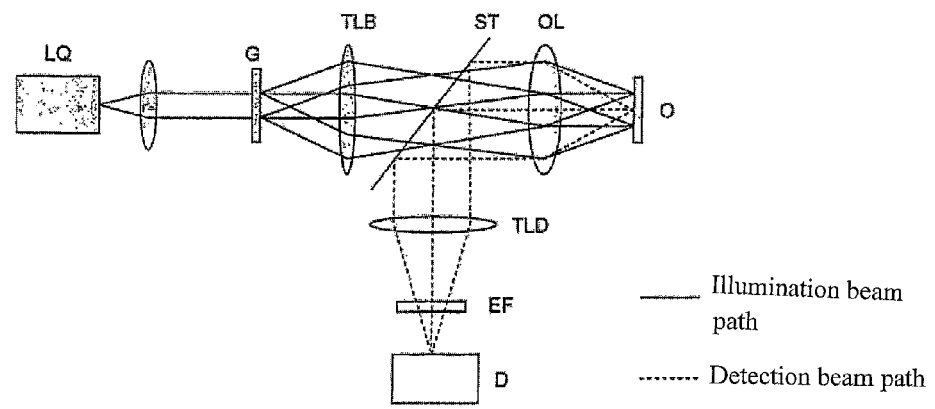
Figure 5: Structured illumination
G:Grating

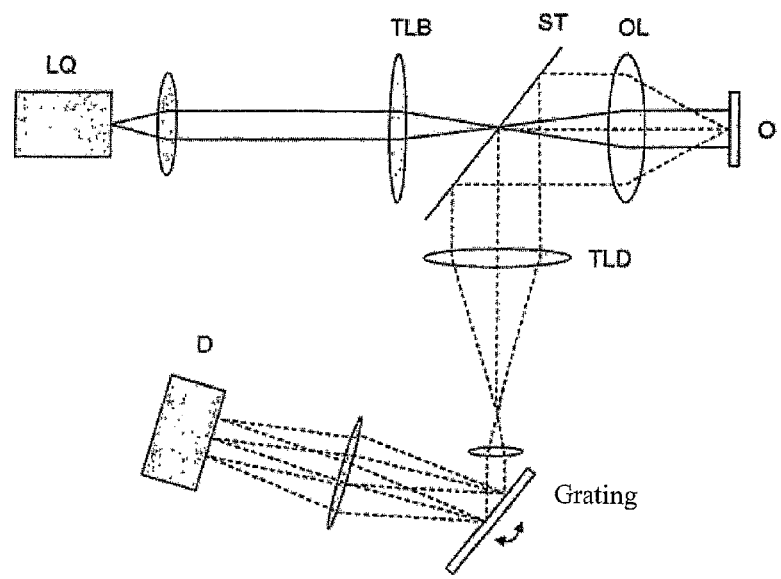
Figure 6: Spectral resolution - grating
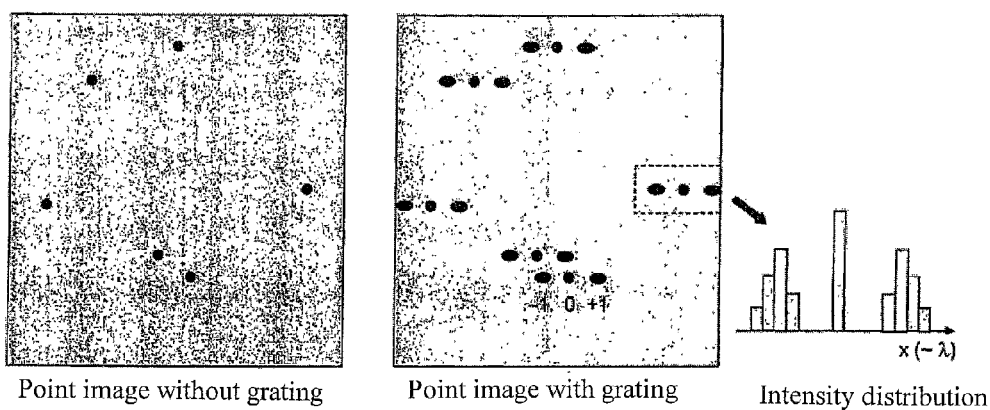
Point image without grating   Point image with grating   Intensity distribution
Figure 6a: Point images for spectral resolution by means of grating

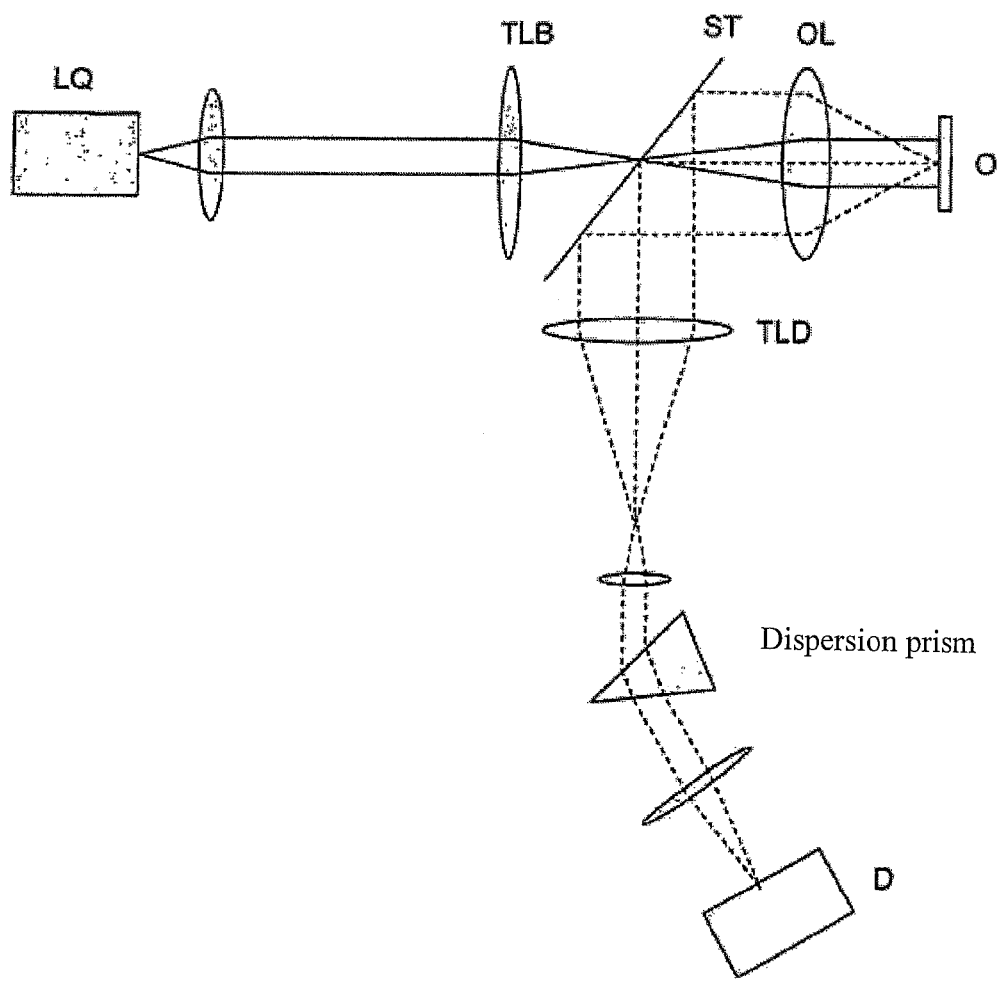
Figure 7: Spectral resolution – prism

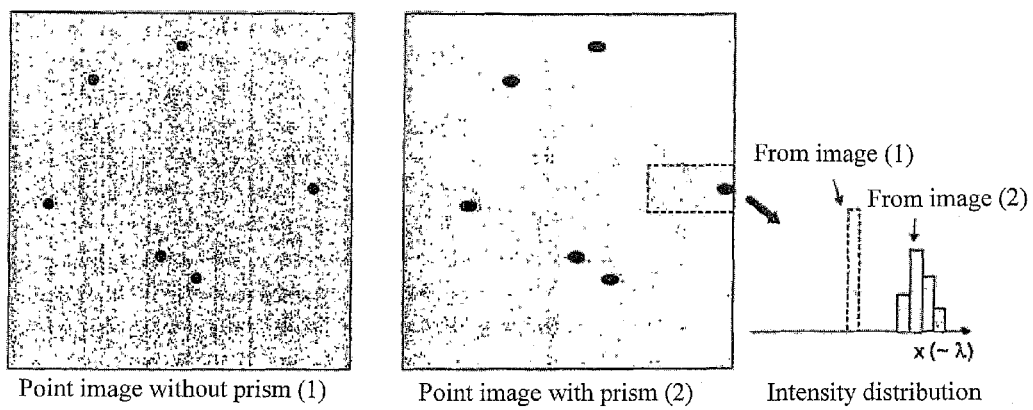
Figure 7a: Point images for spectral resolution by means of prism

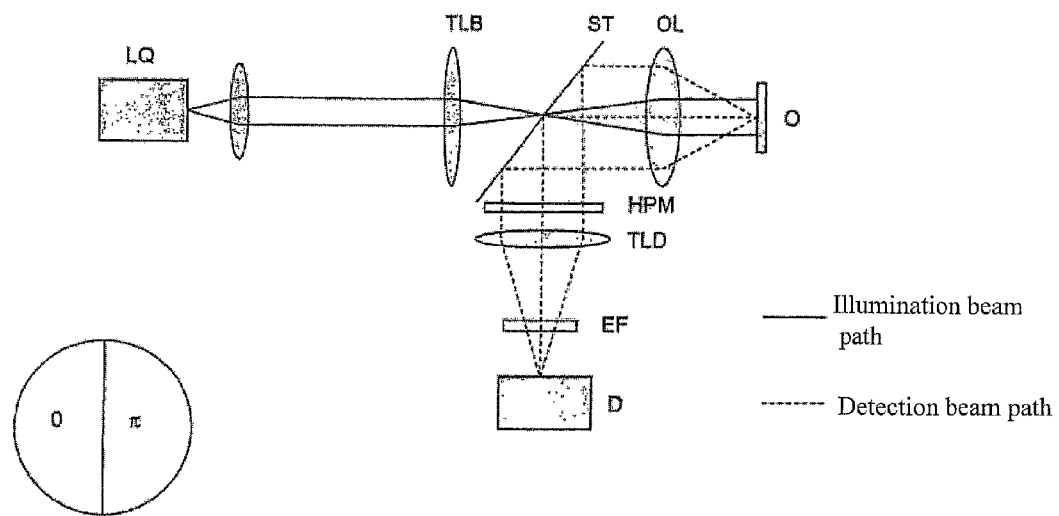
Relative phase delay of π between left and right half space
Figure 8: Double - PSF
HPM:Half space phase mask

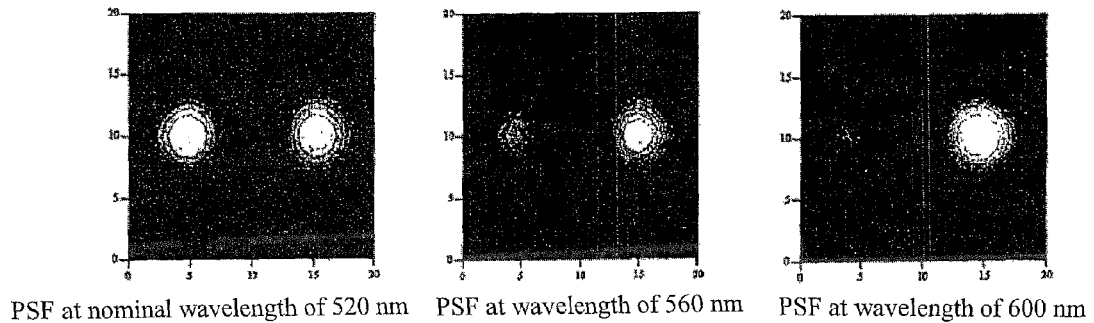
PSF at nominal wavelength of 520 nm    PSF at wavelength of 560 nm    PSF at wavelength of 600 nm
Nominal wavelength = design wavelength of the half space phase mask
Figure 8a: Point image with double - PSF
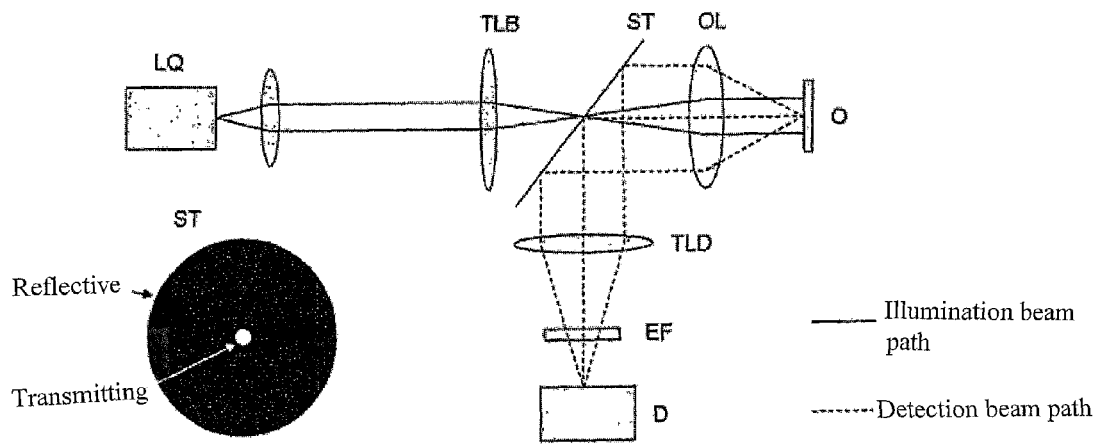
Figure 9: Achromatic beam splitter - far-field illumination

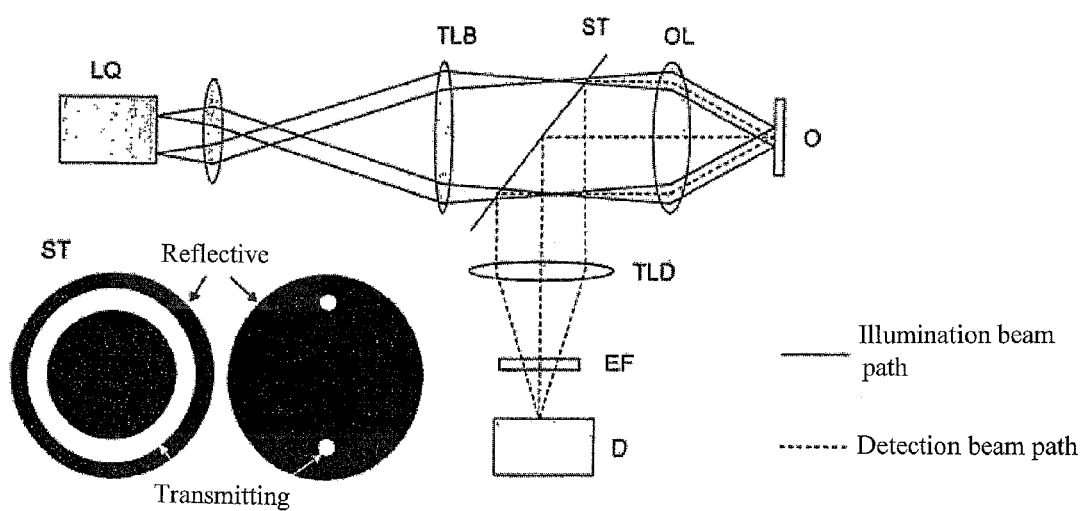
Figure 10: Achromatic beam splitter - TIRF (two alternative variants)

APPARATUS, ESPECIALLY MICROSCOPE, FOR THE ANALYSIS OF SAMPLES

RELATED APPLICATIONS

The present application is a U.S. National Stage application of International PCT Application No. PCT/EP2009/006817 filed on Sep. 22, 2009 which claims benefit of German Application No. DE 10 2008 049 886.6 filed on Sep. 30, 2008, the contents of which are incorporated by reference in their entirety.

BACKGROUND

Resolution-increasing methods in microscopy are known in which the sample is illuminated so that a region is created that can be detected by fluorescence and which is smaller than a region corresponding to the diffraction limit according to Abbe.

This is possible by a non-linear interaction according to various methods:
- Excitation of previously excited molecules by stimulated emission (STED, Klar and Hell, Opt. Lett. 24 (1999) 954-956)
- Excitation of previously excited molecules by further excitation to a higher, non-fluorescent state (Excited State Absorption, Watanabe et al., Optics Express 11 (2003) 3271)
- Depopulation of the ground state by triplet occupation (Ground State Depletion, Hell and Kroug, Appl. Phys. B 60 (1995) 495-597)
- Switching of a dye between a fluorescent state and non-fluorescent state, less fluorescent state, or fluorescent state characterized in some other way (such as, different emission wavelength, polarization) (Hell, Jakobs, and Kastrup, Appl. Phys. A 77 (2003) 859-860)

So-called photo-activation localization microscopy (PAL-M) is based on the possibility of localizing individual molecules with significantly more precision than the full width half maximum of the point-spread function (PSF) when no other emitting molecule is located in the direct neighborhood. This could be guaranteed in optically switchable molecules such that the activation radiation (that sets the molecule into a state suitable for fluorescence excitation) has a suitably low intensity. The excitation radiation then excites only molecules with low density to fluorescence. From the individual PSF imaged on the detector, the locations of the molecules can then be determined with an accuracy limited by the number of photons and the noise. The original state is re-established through the reversible or irreversible switching back to the non-fluorescent excitable state and the process can be repeated until a sufficient, high-resolution image of the sample exists.

The so-called PAL-M method is described in WO2006/127692.

The method involves the photo-activation of individual molecules separated from each other according to the expansion of the detection PSF and their high-precision localization by fluorescence detection.

The PAL-M method as described in WO2006/127692 uses the following primary steps to generate a microscopic image with an optical resolution increased relative to a standard microscope:
1. Photo-activation of individual molecules: Through the activation, the fluorescence properties of the molecules are changed (turning on/off, changing the emission spectrum, . . . ), wherein the activation is performed so that the distance between activated molecules is greater than or equal to the optical resolution of the standard microscope (given by Abbe's resolution limit).
2. Excitation of the activated molecules and localization of the molecules with a spatially-resolving detector.
3. Deactivation of the activated molecules.
4. Repetition of steps 1-3 and superimposition of the localization points from step 2 that were obtained from different iteration steps to form a high-resolution image.

The activation is performed advantageously, but not necessarily, using far-field illumination and has a statistical distribution.

Substances are used (designated as "optical labels") that can be transitioned from an inactive state to an activated state.

These substances, called "PTOL," are activated by a suitable activation radiation. First, the sample is activated such that only a sub-set of the marking molecules in the sample are activated, that is, can emit fluorescence radiation.

Then the excitation radiation is applied to the sample and the fluorescent sample is mapped, wherein the fluorescence radiation can then originate only from the activated sub-set.

After this fluorescence has died down, a new activation is performed that now detects a different sub-set of the PTOL for statistical reasons.

Thus, the set of all marking molecules is divided into different sub-sets that are transitioned one after the other into the state that can be excited to fluorescence. After the excitation, the fluorescence radiation is imaged, advantageously with a sensor array.

A corresponding fluorescence microscope has an excitation light source and also a switching light source that load the sample with corresponding signals.

The sample is imaged by means of an objective lens onto a sensor array.

A computer is provided that actuates the switching light source and the excitation light source by means of control lines.

Here, the activation and excitation can take place in total reflection (FIG. 1, TIRF=total-internal-reflection fluorescence) or in the far field (FIG. 2).

In this method, the resolution is determined above all by the local photon statistics at the location of the molecule. This is related to the total number of detected fluorescence photons, the local intensity, and the background.

An optimization of these statistics through or after the detection leads directly to an improved localization accuracy and thus an improved resolution.

Alternatively, such optimized statistics could allow a quicker image recording at the same resolution.

In addition to the resolution, another important feature is the possibility of detecting several different molecules in one sample. This allows correlations between molecules and structures in the sample to be studied. In order to produce these correlations with a high locational accuracy, a simultaneous detection of the signals on a detector is a preferred solution.

SUMMARY OF THE INVENTION

One object of the present invention is to disclose advantageous solutions for both stated problems, the improved position determination of the molecules by optimization of the local statistics (fluorescence and background photons) and the simultaneous detection of several molecules with one detector.

This is achieved according to the invention advantageously in that, in the beam path, advantageously for detection, a phase mask is provided that generates, in the detector plane, a light distribution (PSF) with at least partially limited, local radiation minimum.

Preferred usable phase masks are spiral phase masks, half space phase masks, as well as other masks with continuous or discontinuous change in phase delay.

In a second advantageous construction, in the beam path, a phase mask or an axicon is provided for generating a Bessel distribution (PSF) in the detector plane.

Advantageously, an additional annular amplitude mask could be arranged between phase mask and detector.

According to the invention it is further provided that, in the illumination beam path, means are provided for the structuring of the illumination distribution.

Such means can consist of phase and/or amplitude gratings or means for the splitting and superimposition of coherent light, so that the structuring is produced by interference in the object plane.

In one method according to the invention, the structuring is shifted continuously or in discrete steps, wherein at least two recordings are realized at different positions of the structuring and a section image is calculated.

According to the invention it is further provided that, in the detection beam path, means are provided for the spectral splitting of the sample light, such as a grating and/or prism.

In one preferred method for a recording (detection) with a grating, the spectral emission center of gravity of the fluorescence is determined from the position and/or the spectral distribution is determined from the shape of the light distribution in one or several higher orders of diffraction.

For a recording with a prism, a separate recording can take place with and without a prism, as well as similarly a determination of the spectral emission center of gravity of the fluorescence from the position and/or determination of the spectral distribution from the shape of the light distribution.

A separation of light distributions superimposed through spectral splitting can take place advantageously through spectral segregation.

According to the invention it is further provided that means are arranged in the detection beam path, with such means causing a color-dependent light distribution (PSF) in the detector plane.

Such means can be optics with chromatic defects, phase masks, half space phase masks, amplitude masks, or also diffractive lenses. According to the invention, a determination of the spectral center of gravity of the emission can take place from the color-dependent PSF, by means of calibrated or calculated light distributions as a function of the wavelength.

According to the invention it is further provided that the sample illumination is focused in one aperture-diaphragm plane and/or in the vicinity of the aperture-diaphragm plane of the beam path between sample plane and detection plane and means are provided in this plane for the spatial separation of the illumination light from the detection light, wherein the means for the spatial separation are made from at least one reflecting first section and at least one transmitting second section, and wherein the reflecting section is used for the coupling of the illumination light and the transmitting section is used for the passage of the detection light in the direction of the detection or the transmitting section is used for the coupling of the illumination light and the reflective section is used for the decoupling of the detection light.

Advantageously, a beam splitter is provided in or in the vicinity of the aperture-diaphragm plane of the microscope objective, wherein this beam splitter has a first small section that has a reflecting or transmitting construction and this beam splitter also has a second larger section that has a transmitting or reflecting construction.

According to the invention it is further provided that a receiver array is formed from position-sensitive receivers (PSD), wherein a reading of position and position accuracy of the light distribution is performed for each element of the array.

EMBODIMENTS

The arrangements are shown below for the most part in far-field illumination. Analogous arrangements apply for the total reflection (TIRF) mode.

BRIEF DESCRIPTION OF THE DRAWINGS

FIG. 1 is a schematic illustration showing a microscope arrangement for TIRF illumination;

FIG. 2 shows an example beam path for far-field illumination;

FIG. 3 illustrates a spiral phase mask arranged downstream of the beam splitter in the direction of the detector in the detection beam path;

FIG. 3a shows the zero points that are produced at the locations of the illuminating points and are surrounded by a ring of intensity;

FIG. 4 shows an axicon APM in an intermediate image in the detection, as well as an annular amplitude mask AM in a 4f arrangement of two transmission lenses in front of the detector;

FIG. 5 is a schematic illustration showing a microscope arrangement with a phase or amplitude grating located in the excitation beam path;

FIG. 6 shows a grating for spectral splitting in the detection beam path;

FIG. 6a shows point images with and without grating;

FIG. 7 illustrates an arrangement with a dispersion prism for the spectral;

FIG. 7a shows point images with and without a prism;

FIG. 8 illustrates an arrangement with a half space mask shown and arranged downstream of the beam splitter in the detection beam path;

FIG. 8a illustrates that the mask acts differently for different wavelengths;

FIG. 9 illustrates an arrangement with an achromatic beam splitter shown in or in the vicinity of the objective aperture diaphragm; and FIG. 10 also illustrates an arrangement with an achromatic beam splitter shown in or in the vicinity of the objective aperture diaphragm in which the beam splitter alternatively has two transparent, small regions at the edge for the illumination beams or an annular, transmitting region on which the arbitrarily oriented illumination beams for the TIRF illumination can be focused.

REFERENCE SYMBOLS

LQ: light source
TLB: tube-body lens illumination
OL: objective lens
O: object
ST: beam splitter
TLD: tube-body lens detection
EF: emission filter
D: detector The following elements are common to the figures below: light source LQ, an illumination-side tube-body lens TLB, an objective OL, the object (sample) O, a beam splitter ST for the separation of illumination and detection light (main dichroic beam splitter), a detection-side tube-body lens TLD, emission filter EF, and also a detector D.

The solid lines represent the illumination beam path, the dashed lines represent the detection beam path.

The illustrated beam profile is an example and could be replaced by other beam paths, in order to represent far-field illumination—and detection, as is familiar to someone skilled in the art, or a confocal beam path of a scanning microscope or a microscope with parallel, confocal illumination and detection as in the use of Nipkow disks.

In the case of PAL-M technology, the preferred construction is currently a far-field arrangement.

DESCRIPTION OF THE EMBODIMENTS

In FIG. 1, as an example for TIRF illumination, two beams are shown that are focused in the rear focal plane of the objective, in a radial position relative to the optical axis, with the result that they are focused at an angle above the TIRF angle (total reflection) in the object carrier (not shown here).

FIG. 2 shows an example beam path for far-field illumination.

In FIG. 3, a spiral phase mask is shown as an example that is arranged downstream of the beam splitter in the direction of the detector in the detection beam path.

One advantageous possibility for the optimization of the local statistics consists in using special PSF's that have advantages in comparison with conventional PSF's for the localization. A preferred PSF in this context is the so-called doughnut PSF, wherein a central zero point in intensity is surrounded laterally by a ring of intensity (FIG. 3a shows the zero points that are produced at the locations of the illuminating points and are surrounded by a ring of intensity).

Through correspondingly constructed phase masks with a change in phase, these PSF's can be generated advantageously.

Through a phase jump on the mask, destructive interference is generated that is surrounded by maxima of constructive interference. See, e.g., DE102006047912A1.

This PSF is preferably realized by a spiral phase mask in the detection beam path with a phase profile $S(\phi)=\exp(-j\phi)$, where $\phi$ is the azimuth angle.

The spiral phase mask essentially influences the lateral structure of the PSF, the axial structure remains essentially unchanged.

The doughnut PSF distinguishes itself in this context by the following properties:
 the doughnut beams are less sensitive, e.g., with respect to spherical aberration that is always present even in optimal optical systems due to small differences in refractive index in the immersion and object and are therefore almost always diffraction-limited,
 the position determination of the zero point is simplified by the symmetry.

For the same number of photons, these properties make a more precise localization possible. The doughnut PSF's or related PSF's with a zero point at the localization position can also be achieved by other masks that are incorporated in the disclosure.

The mask could be in the vicinity of the aperture diaphragm but also at any other arbitrary location (FIG. 3). Other phase masks (such as a ring phase mask) change both the axial and also the lateral structure—generation of a three-dimensional zero position.

Other special PSF's are so-called Bessel beams that can be achieved through special axicon phase masks (FIG. 4). See, e.g., US 2005/0046818A1.

An example profile I of such a mask is $S(r)=\exp(-jr)+\exp(jr)$, where r is the radial coordinate in the beam. This mask should be in or in the vicinity of an intermediate image and generates an annular illumination of the aperture diaphragm.

In FIG. 4, an axicon APM is shown in an intermediate image in the detection, as well as an annular amplitude mask AM in a 4f arrangement of two transmission lenses in front of the detector.

In contrast to US 2005/0046818A1, the phase mask is here located in the detection beam path. In order to avoid light losses, an optional annular amplitude mask that could be used for improving the axial homogeneity of the PSF (US 2005/0046818A1) could be in the beam path between phase mask and detector (FIG. 4).

By means of the ring mask (amplitude mask), a fine adjustment of the distribution is achieved; an especially homogeneous distribution is achieved in the axial direction by cutting away secondary maxima.

The PSF imaged on the detector has the following advantageous features:
 the focal depth of the image is expanded, wherein a high-resolution "projection image" is produced across a relatively large focal depth of field;
 the maximum of the distribution is about 30% narrower than for a conventional PSF, which balances out, at least partially, the reduced intensity in maximum; and
 the PSF has a typical space frequency spectrum (suppression of lower space frequencies) that allows an effective background suppression to be achieved before position determination by adapted filtering of the low-frequency portion in the images in the Fourier domain.

Also in other PSF's, background suppression can be achieved by a filtering optimally adapted to the PSF of low frequency spatial frequencies, which is part of this invention application. However, this filtering is especially effective for PSF's that have a large portion of high spatial frequencies similar to the Bessel beams. The optimal filtering here should also take into account the spatial frequency spectrum of the background that could be obtained at a suitable position in the image (without molecules to be localized) or from a subset of recorded and optionally partially calculated images. In the simplest case, the filter is then the inverse spectrum of the background.

A suppression of the background based on a similar principle can be achieved through structured illumination. Here, for example, a phase or amplitude grating is located in the excitation beam path (FIG. 5).

Alternatively, a structured illumination could also be generated by the splitting and superimposition of coherent light in the object plane by means of interference. If the structuring is moved during the illumination, the emission of the molecules located at the focus changes ("blinking").

In contrast, the portions that are out of focus remain essentially unchanged. A recording of at least 2 images for each activation cycle and the consideration of the modulated signal portion therefore allow efficient background suppression.

The individual points are modulated by shifting from light to dark and the blinking of the PSF is recorded as a signal.

One advantageous embodiment is a continuous shifting of the grating.

When recording, for example, 3 images with different phase positions (see, e.g., WO97/06509, WO98/45745, DE10155002A1), the known calculation is carried out from the individual images.

The shifting of the grating is advantageously linked in time to the activation cycle (synchronized), within an activation cycle, for example, 2 or 3 recordings would then be made with shifted grating and then a new activation cycle would be initiated.

One potential problem could be the read-out rate of the camera being limited by the data transfer. This problem could be solved in advance by a camera that has a significantly lower pixel count than is known from a conventional camera. Because only a small number of illuminating molecules is to be detected in each image, in the case of PAL-M, in principle, a reduced pixel count is sufficient. However, the localization requires good scanning of the PSF. Alternatively, each of the (few) pixels could be constructed as a position-sensitive receiver. This could be, e.g., a two-dimensional array of position-sensitive diodes (PSD) known from the prior art. Because the surfaces of such PSD's are large in comparison with conventional camera pixels, the image enlargement must be selected with a corresponding size. By means of CMOS technology, however, special arrays could also be produced with small pixel sizes. With integrated evaluation electronics, the data transfer load could then be limited to a few parameters (such as the center of gravity of the distribution and a measure for the position accuracy=3 parameters) for each molecule, and thus could be reduced dramatically. A prerequisite, however, is that, on the statistical mean, only one illuminating molecule is to be imaged on each pixel. Because the prerequisite for PAL-M imaging is that two excited molecules lie spaced apart from each other by more than the full width at half maximum (FWHM) of the conventional PSF, a pixel size that corresponds approximately to twice the FWHM is conceivable. Because sampling must be performed at least according to the Nyquist theorem according to the prior art (i.e., two pixels per FWHM in both lateral directions), in the above case, at least a 4×4=16 times reduction of the pixel count, and at least 16/3=5 times reduction of the data quantity and thus an at least 5 times speed increase can be achieved.

The optimal background suppression prevents the detection of the background, so that both the associated noise is completely missing in the image and also the dynamic response of the detector can be optimally used. Such a possibility consists in the combination of activation in the far field with parallel-confocal detection as can be achieved with Nipkow disk scanning or line scanning.

The detection of several different molecules simultaneously with one detector is based on the spectral differentiation of the fluorescence of the different dye molecules. In particular, in the case of PAL-M, one can take advantage of the fact that individual molecules are detected separately. This opens up possibilities for the spectral separation of the molecules on one detector.

In FIG. 6, a grating G for spectral splitting in the detection beam path is shown.

In FIG. 7, a dispersion prism for the spectral splitting is shown.

By means of a spectrally splitting element (such as e.g., grating, prism) in the collimated detection beam path, PSF's whose position depends on the spectral composition of the fluorescence can be imaged on the detector.

For a grating, e.g., a PSF at the location of the 0th order (corresponds to the position without a grating) and two other (slightly split) at the location of the ±1st order are detected (FIGS. 6, 6a).

Through another recording without a grating, the 0th orders can be determined separated from the 1st orders. From the spacing of the 0th and ±1st orders, according to the corresponding calibration of the spectral center of gravity, the spectral distribution can be determined from the shape of the spectrum of the 1st order.

Another possibility consists in directly seeking and evaluating symmetric distributions of the 0th and the two first orders on the detector.

Because the fluorescence spectra are typically spectrally wideband, that is, the recorded points have a certain extent, as a rule the 0th (not widened) can also be separated from the ±1st orders from one recording.

One preferred grating here diffracts with high efficiency in the 0th and ±1st orders and negligibly in higher orders.

For the use of a prism that can be advantageous for reasons of efficiency, in advance only one order appears (FIGS. 7, 7a). Here, at least 2 measurements are required at different positions of the prism (or preferably one additional measurement with pivoted prism), in order to achieve a unique allocation of the image points and the spectral splitting. Here, the spectrum could also be obtained from the shape of the spectrally split distribution in the image.

It can occur that two molecules are indeed sufficiently separated from each other spatially without spectral splitting and superimposition is created by the spectral splitting. Here, with knowledge of the spectral properties of the dyes or determination of the spectral properties from other regions of the image, for example, also of another diffraction order, a separation can be achieved through spectral segregation by means of image processing and spectra can be allocated unambiguously to molecules.

A direct-vision prism represents one special case. Here, the light is similarly spectrally split but symmetrically about the nominal position of the molecule. Advantageously, for the most part, one image recording is sufficient.

Similarly, the spectral dependency of the shape of the PSF can be used to perform the spectral separation. In particular, PSF's generated with the help of phase masks have a very strong dependency. One example is the doughnut PSF that is generated with a spiral phase mask. One special advantage is the primary wavelength dependency of the lateral distribution. Another example is a mask with a phase jump of $\pi$ in the half space, which leads to a double PSF (FIG. 8).

In FIG. 8, the half space mask HPM is shown and arranged downstream of the beam splitter in the detection beam path.

The spectral variation can be calibrated and taken into consideration for the evaluation (FIG. 8a). This means that the mask acts differently for different wavelengths.

Far away from the designated wavelength, the effect fades away; only "normal" PSF is generated.

The transition from the double to the single PSF can be calibrated, and the wavelength distribution can be determined from the present distribution. Other elements, such as diffractive elements, are also advantageously conceivable that influence the shape of the PSF as a function of the wavelength.

In addition to phase elements, amplitude elements (or elements with phase and amplitude variations) could also introduce a wavelength dependency that can be utilized in the designated sense. A typical representative is, for example, a diffractive lens that introduces, in combination with a microscope objective (hybrid objective) a chromatic defect that could be used for spectral coding.

In order to excite and to detect different molecules, beam separation that is as achromatic as possible for excitation and detection is required. Therefore, due to the activation and excitation in the far field, the use of an AchroGate beam splitter (See, e.g., DE10257237A1) is advantageous. This allows a high-efficiency and completely flexible separation of the beam paths, e.g., also for simultaneous excitation with different wavelengths (FIGS. 9 and 10).

In FIGS. 9 and 10, an achromatic beam splitter according to DE10257237A1 is shown in or in the vicinity of the objective aperture diaphragm.

In one embodiment for the far-field illumination, it is provided as shown in FIG. 9 with a central, small transmitting region onto which focusing is performed on the illumination side, and has a large reflective region for transmission of almost the entire detection light in the direction of the detector D.

In FIG. 10, the beam splitter alternatively has two transparent, small regions at the edge for the illumination beams or an annular, transmitting region on which the arbitrarily oriented illumination beams for the TIRF illumination can be focused.

The other reflective region is used, in turn, for the mirroring of the sample light in the direction of the detection.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

The invention claimed is:

1. A microscope device comprising a diffraction-limited resolution volume with several dye molecules that can be switched between different states, wherein at least one state is fluorescent, the fluorescence is collected with an objective lens (O), and imaged by an optical system onto a spatially-resolving detector,
   wherein the dye molecules have in at least one portion of the sample, a distribution density that is greater than the inverse of the diffraction-limited resolution volume,
   one or more light sources for the emission of switching radiation, in order to switch a first sub-set of the dye molecules have in the sample and for the emission of excitation radiation, in order to excite the first sub-set of the dye molecules,
   wherein, a phase mask is provided in a beam path of detection radiation that generates, in the detector plane, a light distribution with at least partially limited, local radiation minimum, by destructive interference, said light distribution being surrounded by constructive interference maxima, said phase mask having a continuous or discontinuous change in phase delay.

2. The device of claim 1, wherein the switching is a photo-activation or deactivation of the dye molecules.

3. The device of claim 1, wherein an actuation device is provided for the control of the switching radiation, in order to ensure that the distribution density of the dye molecules located in the fluorescent state is less than the inverse of the diffraction-limited resolution volume of the device.

* * * * *